(12) United States Patent
Masala et al.

(10) Patent No.: US 8,647,290 B2
(45) Date of Patent: Feb. 11, 2014

(54) HEMODIALYSIS OR HEMO(DIA)FILTRATION APPARATUS AND A METHOD FOR CONTROLLING A HEMODIALYSIS OR HEMO(DIA)FILTRATION APPARATUS

(75) Inventors: Pietro Masala, Latina (IT); Mauro Suffritti, Medolla (IT); Anders Wallenborg, Bjärred (SE); Thomas Gebhart, Lully (CH)

(73) Assignee: Gambro Lundia AB, Lund (SE)

( * ) Notice: Subject to any disclaimer, the term of this patent is extended or adjusted under 35 U.S.C. 154(b) by 330 days.

(21) Appl. No.: 12/994,383

(22) PCT Filed: May 26, 2008

(86) PCT No.: PCT/IB2008/001308
§ 371 (c)(1),
(2), (4) Date: Nov. 23, 2010

(87) PCT Pub. No.: WO2009/144522
PCT Pub. Date: Dec. 3, 2009

(65) Prior Publication Data
US 2011/0098625 A1  Apr. 28, 2011

(51) Int. Cl.
| A61M 1/34 | (2006.01) |
| A61M 1/14 | (2006.01) |
| A61M 1/16 | (2006.01) |
| A61M 5/142 | (2006.01) |

(52) U.S. Cl.
USPC ....... 604/6.09; 604/4.01; 604/5.01; 604/6.11; 422/44

(58) Field of Classification Search
USPC ................ 604/4.01, 5.01, 6.09, 6.11; 422/44
See application file for complete search history.

(56) References Cited

U.S. PATENT DOCUMENTS

| 5,660,722 | A | * | 8/1997 | Nederlof ..................... 210/90 |
| 5,762,805 | A | * | 6/1998 | Truitt et al. .................. 210/645 |
| 6,083,187 | A | | 7/2000 | Nakayama et al. |
| 2001/0007930 | A1 | * | 7/2001 | Kleinekofort ............... 604/4.01 |
| 2001/0045395 | A1 | | 11/2001 | Kitaevich et al. |
| 2003/0130608 | A1 | * | 7/2003 | Pfeil et al. ................... 604/5.01 |
| 2004/0030277 | A1 | * | 2/2004 | O'Mahony et al. ......... 604/4.01 |
| 2004/0068219 | A1 | * | 4/2004 | Summerton et al. ........ 604/5.01 |
| 2005/0061740 | A1 | | 3/2005 | Felding et al. |
| 2005/0065459 | A1 | | 3/2005 | Zhang et al. |

(Continued)

FOREIGN PATENT DOCUMENTS

| EP | 1 110 566 A2 | 6/2001 |
| EP | 1 283 064 A2 | 2/2003 |

(Continued)

OTHER PUBLICATIONS

Gambro Lundia AB, AK 200 Maintenance Manual, p. 2:26 (2001).

(Continued)

Primary Examiner — Adam Marcetich
(74) Attorney, Agent, or Firm — Pearne & Gordon LLP

(57) ABSTRACT

In a hemodiafiltration apparatus, a control and command unit (11) halts a replacement fluid supply pump (8) and contemporaneously modifies the control mode of a blood pump (1) passing from a control based on the pump velocity to a control based on the blood pressure measured by a sensor (12) arranged downstream of a hemodiafilter (3). The aim is to prevent risks due to excessive hemoconcentration in the blood circuit between the ultrafiltration zone and the infusion zone.

20 Claims, 3 Drawing Sheets

(56) References Cited

U.S. PATENT DOCUMENTS

| | | |
|---|---|---|
| 2005/0230313 A1* | 10/2005 | O'Mahony et al. ............ 210/645 |
| 2006/0074369 A1* | 4/2006 | Oishi et al. ................... 604/4.01 |
| 2006/0254982 A1 | 11/2006 | Kopperschmidt |
| 2007/0066928 A1 | 3/2007 | Lannoy |
| 2008/0177216 A1* | 7/2008 | Ash .............................. 604/6.11 |
| 2008/0195022 A1* | 8/2008 | Lucke et al. ................. 604/4.01 |
| 2008/0215247 A1 | 9/2008 | Tonelli et al. |
| 2008/0275377 A1* | 11/2008 | Paolini et al. ................ 604/6.11 |
| 2009/0099406 A1* | 4/2009 | Salmonsen et al. ............. 600/17 |

FOREIGN PATENT DOCUMENTS

| | | |
|---|---|---|
| EP | 1 450 880 | 9/2004 |
| EP | 1 595 560 A1 | 11/2005 |
| WO | 03/028860 A1 | 4/2003 |
| WO | 03/047656 A1 | 6/2003 |
| WO | 03/082144 A2 | 10/2003 |
| WO | 2006/011009 A2 | 2/2006 |

OTHER PUBLICATIONS

Gambro Lundia AB, AK 200 Replacements, p. 3:3 (1999).

Gambro Lundia AB, Service Technicians Guide, pp. 4:13 and 4:19 (1999).

Gambro Lundia AB, Technical Description Fluid Monitor, pp. 5:5, 5:7, and 5:12 (1999).

Gambro Lundia AB, BiCart Select System, pp. 10:5 and 10:6 (1999).

* cited by examiner

HEMODIALYSIS OR HEMO(DIA)FILTRATION APPARATUS AND A METHOD FOR CONTROLLING A HEMODIALYSIS OR HEMO(DIA)FILTRATION APPARATUS

BACKGROUND OF THE INVENTION

The invention relates to a hemodialysis or hemo(dia)filtration apparatus and a method for controlling the apparatus.

Specifically, though not exclusively, the invention can be usefully employed in any hemodialysis or hemo(dia)filtration apparatus of known type, for example for chronic therapy and/or intensive therapy.

Reference is made in particular to a hemo(dia)filtration at least in post-dilution, i.e. with replacement fluid infusion at least downstream of the semipermeable membrane treatment device (hemo(dia)filter). The present invention can also be applied in hemo(dia)filtration combined with pre- and post-dilution, and in hemo(dia)filtration in mid-dilution, i.e. with replacement fluid infusion between two semipermeable membrane treatment devices arranged consecutively.

As is known, in hemo(dia)filtration a part of the impure plasmatic liquid making up the extracorporeal blood is ultra-filtered through a semipermeable membrane and replaced with the pure replacement fluid. The known art comprises various hemo(dia)filtration systems in which a replacement fluid supply line is connected to a blood circuit downstream of a membrane treatment device. In these systems, when the replacement fluid supply is stopped, there is a tract of extracorporeal circuit (comprised between the membrane and the infusion point) which exhibits very dense blood, being divested of a part of the plasmatic liquid. This leads to the risk of an excessive and undesired increase of the blood pressure in the circuit.

The prior art comprises a hemo(dia)filtration system, known as Gambro® AK 200™, in which on halting the post-dilution flow, the control unit automatically increases the maximum safety value of the venous pressure for a determined period of time, such as to prevent signalling by an alarm due to the fact that it passed beyond the upper limit of the safety range of the venous pressure.

There are also various types of blood treatment systems in which a blood pump is controlled in order to prevent an excessive raising of the extracorporeal blood pressure.

In U.S. Pat. No. 6,083,187, for example, a blood pump is controlled such that the pressure measurements for the blood collection pressure, venous blood pressure and the difference of pressure across a plasma separator do not exceed the respective values.

In EP 1283064, in order to make a further example, a plasma supply pump is controlled in reference to a plasma inlet pressure so that the pressure falls within a predetermined range with respect to a preset pressure value.

EP 1110566 shows a further example in which an extracorporeal treatment system comprises a controller which operates a pump on the basis of a comparison between a measured pressure value and a threshold value.

In WO 03/082144 a blood pump is controlled on the basis of a pressure value in the extracorporeal circuit.

WO 03/028860 describes a hemo(dia)filtration system which comprises automatic passage from a control of a first parameter (for example the blood flow) to the control of a second parameter (for example the blood pressure) when the blood pressure passes out of a respective range of acceptable values.

SUMMARY OF THE INVENTION

An aim of the present invention is to provide a hemodialysis or hemo(dia)filtration system in which the sudden variation (e.g. absence or reduction or presence or increase) of an infusion flow (e.g. a flow of replacement fluid in hemo(dia)filtration treatment or a flow of an infusion bolus in hemodialysis or hemo(dia)filtration treatment) downstream or upstream of the hemodialyser or hemo(dia)filter does not cause an undesired situation.

A further aim of the invention is to realise a control method for a hemodialysis or hemo(dia)filtration system which prevents an undesired situation in a case of a sudden variation (e.g. absence or reduction or presence or increase) of an infusion flow (e.g. a flow of replacement fluid in hemo(dia)filtration treatment or a flow of an infusion bolus in hemodialysis or hemo(dia)filtration treatment) downstream or upstream of the hemodialyser or hemo(dia)filter.

An advantage of the invention is to provide a hemo(dia)filtration system and a relative control method which reduce the risks due to an undesired situation as a consequence of a high hemoconcentration in at least a tract of the extracorporeal circuit, in particular in the tract comprised between the ultrafiltration zone and the dilution zone located downstream of the above-mentioned ultrafiltration zone.

A further advantage is to make available a hemo(dia)filtration system and a relative control method which enable passage from a therapy with post-dilution (and/or pre/dilution) of the replacement fluid to a therapy without post-dilution (and/or pre/dilution), without generating undesired phenomena in the transition period, such as for example excessive hemoconcentration in a tract of the blood circuit, excessive increase of pressure in the venous branch of the blood circuit, the setting-off of alarms for exceeding the maximum safety threshold of the venous pressure, the blocking of the therapy due to the setting-off of an alarm, and so on.

A still further advantage is that the invention provides a hemodialysis or hemo(dia)filtration system which is constructionally simple and economical and, further, provides a safe and reliable control method for the system.

These aims and more besides are all attained by the present invention, as it is characterised in one or more of the appended claims.

Further characteristics and advantages of the present invention will better emerge from the detailed description that follows, of at least a preferred embodiment, illustrated by way of non-limiting example in the accompanying figures of the drawings.

BRIEF DESCRIPTION OF THE DRAWINGS

The description will be made herein below with reference to the accompanying figures of the drawings, provided by way of non-limiting example.

DETAILED DESCRIPTION

Figure 1:
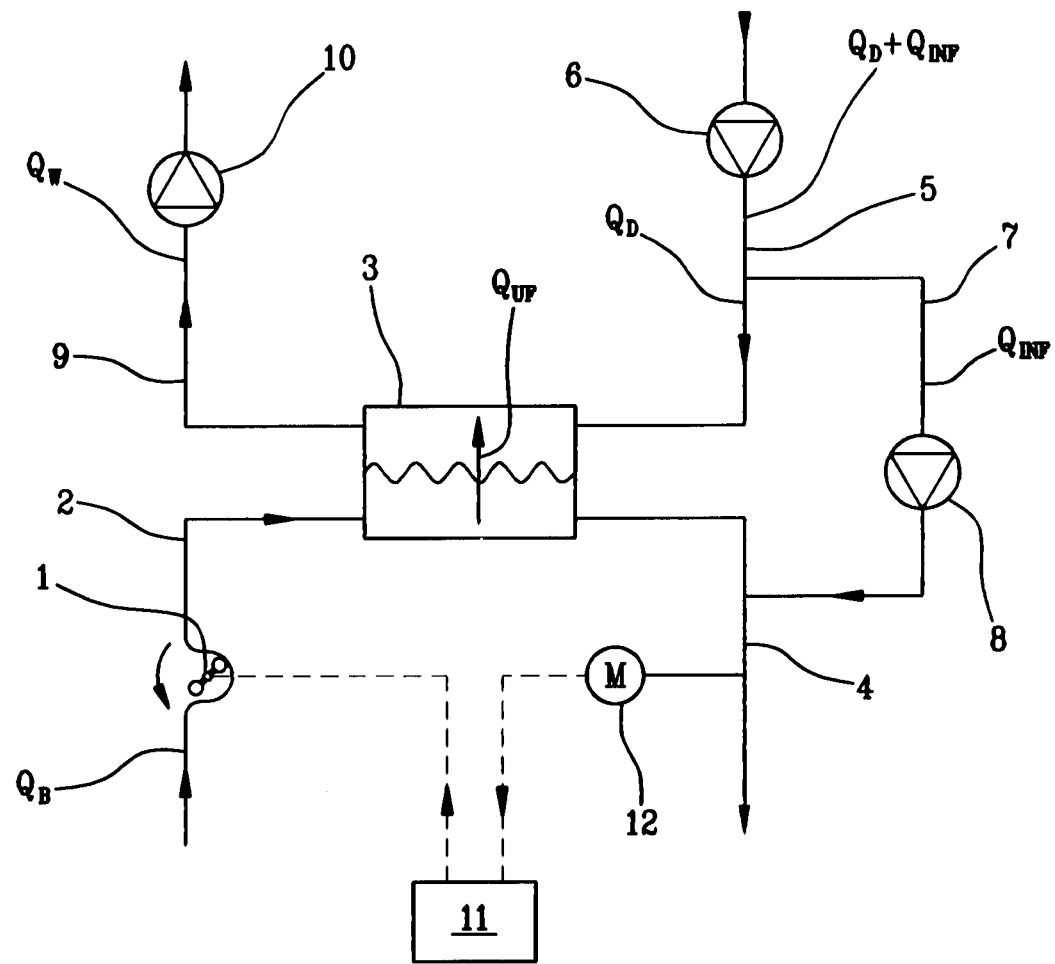
FIG. 1 is an hemodiafiltration apparatus according to the present invention.

With reference to FIG. 1, 1 denotes a blood pump, 2 an arterial line, 3 a hemodiafilter, 4 a venous line, 5 a dialysis fluid supply line, 6 a dialysis fluid supply pump, 7 a replacement fluid supply line, 8 a replacement fluid pump, 9 a used fluid discharge line, 10 a used fluid drainage pump, 11 a control unit and 12 a venous pressure sensor.

The blood pump 1 can comprise any blood pump of known type. The blood pump 1 can be, as in the illustrated example, a flexible-wall deformation pump, for example a peristaltic pump, optionally a rotary pump. The blood pump 1 can comprise, for example, a volumetric pump, a positive-displacement pump, a membrane pump, a piston pump or any other actuator of known type, usable for extracorporeal blood transport. The blood pump 1 can be arranged, as in the illustrated example, along the arterial line 2 or along the venous line 4. It is possible to use a pump on the arterial line and a further pump on the venous line.

The arterial line 2 can be provided with one or more elements, of known type, used in an arterial line of an extracorporeal blood circuit, such as for example a dialysis set. The known elements can comprise, for example, one or more of the following elements: a patient connector (for example a luer connector) for removably connecting to a patient's vascular device, an access site for removal or injection of substances from or into the circuit, a gas-liquid separation chamber (air-blood) before and/or after the blood pump 1, an anticoagulant infusion line, an arterial clamp for blocking the flow, a pressure sensor arranged before and/or after the blood pump 1, a priming line branching on the arterial line, one or more service lines (for example for predisposition of a pressure sensor or a transducer-protector device, for removing or introducing fluids, for adjustment of the liquid level in the separation chamber, etc.), a filter connector (for example a luer connector) for removable connection with an access port of the hemodiafilter 3, a hematocrit sensor or a blood volume sensor, etc.

The hemodiafilter 3 can comprise any one of the known hemodiafilters. The hemodiafilter 3 has a blood chamber and a fluid chamber which are separated from one another by a semipermeable membrane. The blood chamber is part of the extracorporeal blood circuit, exhibiting a blood inlet connected to the arterial line 2 and a blood outlet connected to the venous line 4. The fluid chamber has a dialysis fluid inlet connected to the supply line 5 and a used fluid outlet connected to the discharge line 9.

The hemodiafiltration apparatus comprises a dialysis fluid source (of known type and not illustrated) which can comprise any source of known type. The source can comprise, for example, a batch container of the dialysis fluid, or can comprise a device for in-line preparation of the dialysis fluid starting from water and concentrates. The pump 6 can comprise any pump used in a dialysis circuit for moving a fluid, such as for example a gear pump, a peristaltic pump, or any other volumetric pump or positive displacement pump. The supply line 5 optionally comprises an ultrafilter (known and not illustrated) configured for purification of the dialysis fluid before it reaches the treatment zone (hemodiafilter 3). The supply line 5 can comprise various other elements (actuators and sensors) used in known-type dialysis fluid supply lines, such as for example one or more of the following: one or more pressure sensors, at least a conductivity sensor, at least a pH sensor, at least a temperature sensor, one or more gas-liquid separation devices, a heater, one or more by-pass lines of the hemodiafilter 3, one or more by-pass valves, at least a hydrophobic filter and a connection valve to the atmosphere, at least a dialysis fluid block valve (for example arranged downstream of the replacement fluid line, such as to make possible a selection of various operating modes at the control unit 11, among which for example hemodiafiltration, hemofiltration and hemodialysis), and so on.

The used fluid discharge line 9 can comprise any combination of the elements used in the discharge lines of the hemo(dia)filtration and hemodialysis apparatus of known type, such as for example one or more of the following elements: a pressure sensor, a weight loss line for the passage of the patient weight loss flow, a weight loss pump for controlling the flow of weight loss, a heat exchanger for recuperating a part of the heat of the used fluid, etc.

The replacement fluid supply line 7 can be, as in the illustrated example, a branching of the dialysis fluid supply line 5 (branching arranged after or at the ultrafilter (if present) on the supply line 5). The replacement fluid supply line can comprise, however, any of the replacement fluid lines used in the prior art, such as for example a line connected to a batch source of the replacement fluid. The supply line 7 can optionally comprise an ultrafilter (of known type and not illustrated) configured for the purification of the replacement fluid before reaching the extracorporeal blood circuit. The supply line 7 can further and optionally comprise other usable elements, in a known way, in a replacement fluid supply line, such as for example a gas-liquid separation chamber, one or more service lines for introduction or extraction of fluids, a pressure sensor, a branch line for sending the replacement fluid (or a part thereof) to the arterial line in pre-dilution (with possible predisposition of a control device of the replacement fluid distribution between the arterial line 2, in predilution, and the venous line 4, in post-dilution, which control device can comprise, for example, a valve system or a further replacement fluid control pump cooperating with the pump 8) etc.

During a hemodiafiltration treatment stage, the control unit 11 governs the pumps 6, 8 and 10 such as to obtain a desired flow rate $Q_D$ of the dialysis fluid at the inlet of the hemodiafilter 3 fluid chamber and a desired flow rate $Q_{INF}$ of the replacement fluid sent to the extracorporeal circuit. In general the control unit 11 is also aware of a desired flow rate $Q_{WL}$ of the patient weight loss, on the basis of which it calculates a desired flow rate $Q_{UF}$ (where $Q_{UF}=Q_{INF}+Q_{WL}$) of ultrafiltered liquid through the semipermeable membrane of the hemodiafilter 3. In this way the plasmatic liquid (impure) which is removed for ultrafiltration in the hemodiafilter is replaced by the replacement fluid (pure), taking account of the desired weight loss of the patient. The flow rate $Q_W$ of the used fluid along the discharge line 9 will therefore be $Q_W=Q_D+Q_{INF}+Q_{WL}$. During a stage of hemofiltration treatment, the flow rate $Q_D$ will be zero. During a hemodialysis stage, the flow rate $Q_{INF}$ will be zero.

The hemodiafiltration apparatus is provided with a fluid balance control system configured such that the quantity of blood to be purified removed from the patient through the arterial line 2 is equal (minus the desired weight loss) to the quantity of purified blood returned to the patient via the venous line 4. The control system of the balance fluid can comprise any one of the systems used for this purpose in the prior art in dialysis and/or hemo(dia)filtration apparatus, such as for example a system using weight sensors (for example applied to batch containers of the various fluid used: dialysis fluid, replacement fluid, used fluid), flow sensors (for example coriolis flow meters, geared sensors, magnetic sensors, etc.) applied, for example, to the lines 5 and 9 and possibly also to line 7, volumetric chambers for fluid balancing provided with valves for alternatingly opening and closing the chambers, or other systems besides.

The control of the flows along the supply line 5 and the discharge line 9 can be done according to any one of the control criteria used in the hemodiafiltration apparatus of known type, such as for example a control having a first set point value equal to a desired transmembrane pressure TMP- $_{DES}$ (where the transmembrane pressure is the pressure difference between the two opposite sides of the semipermeable membrane of the hemodiafilter 3) and a second set point value which is equal to a desired flow rate (for example the flow rate $(Q_D+Q_{INF})_{DES}$ of the supply pump 6), or two set point values corresponding to two desired values of two flow rates (for example the flow rates of the pumps 6 and 10 measured by two flow meters) etc.

During a regular (and not transitory) stage of hemo(dia) filtration treatment, in which the replacement flow in post-dilution caused by the pump 8 follows a predetermined progress, for example constant or according to a predetermined profile or another automatic control criterion, the blood pump 1 can be controlled such that the blood flow has a predetermined value. In other words, the blood pump 1 can be controlled on the basis of a set point value corresponding to an operating speed (typically a rotation velocity of a rotor) of the pump itself, or a flow rate value of blood along the extracorporeal circuit measured with an appropriate sensor. Generally an encoder is used, which determines the rotation speed of the rotor of the pump 1, the effective blood flow rate along the extracorporeal circuit being a function of this velocity and other parameters (among which, for example, the cubic capacity of the pump 1 if it is a volumetric pump).

When, for any reason (for example because the operator has selected a different operating mode passing from a hemodiafiltration to a hemodialysis operating mode; or because the dialysis and replacement fluid supply has been interrupted for resons of safety, for example and alarm due to unsuitable values of conductivity and/or the temperature of the dialysis fluid; or because the replacement fluid source comprises an empty batch source; or for other reasons besides), the replacement fluid flow is interrupted or in any case reduced sharply, a particular critical situation occurs in which a part of the extracorporeal blood (the part, that is, which is interposed between the ultrafiltration zone in the hemodiafilter and the post-dilution zone located at the end of the replacement line 7 or the replacement fluid is mixing with the blood), is at a high hemoconcentration degree (i.e. with a low percentage of plasmatic liquid), because it has been ultrafiltered, and proceeds in its extracorporeal circuit in that highly hemoconcentrated state even beyond the post-dilution zone, as the post-dilution flow has totally or partly and suddenly stopped.

The control unit 11 is programmed to intervene at (nearly) onset of the above-described potentially critical situation, by changing the operating mode of the blood pump 1. In particular, the control unit 11 is programmed to control the blood pump 1, using, as the set point value, a predetermined value of venous pressure, so that the control unit 11 receives the pressure signal from the venous sensor 12, compares it with the set point value and thus regulates the blood pump 1 such as to maintain the real venous pressure at the desired value: specifically, if the effective pressure measured is greater than the desired pressure, the blood pump speed will be slowed down, and vice versa. This control mode of the blood pump 1 on the basis of the venous pressure 12 (control mode in safe conditions during a transitory stage of the apparatus) can continue, for example, up till when the operator sends a suitable command, returning to the control mode based on the flow or velocity of the pump; this system can be used, optionally, when the potentially critical situation which determined passage to the mode based on the venous pressure, had been caused by an alarm situation. This control mode of the blood pump 1 on the basis of the venous pressure 12 can continue, in another example, after a predetermined time period has passed; this system can be used, optionally, when the above-mentioned potentially critical situation which had caused the passage into the mode based on the venous pressure, had been caused by the intentional change from a hemo(dia)filtration treatment to a hemodialysis treatment; in this case the period of time is predetermined such that the hemoconcentrate part of the blood is no longer present in the extracorporeal circuit or, however, no longer constitutes a risk. This predetermined period of time can be, for example, a few seconds, or some tens of seconds, or a few minutes, according to the various parameters which influence the potentially critical/undesired situation (e.g. high hemoconcentration), such as for example the configuration (structure, conformation, arrangement, length and diameter of the tubes, volume of the chambers, etc.) of the various elements which form the extracorporeal blood circuit and the infusion circuit, the hemoconcentration of the blood in the hemodiafilter, etc.

When the control mode of the blood pump 1 in safe condition (retroaction control based on the pressure in the blood circuit) is finished, the blood pump 1 can continue to be controlled on the basis of the criterion which it had before the onset of the potentially dangerous situation, or following a different criterion.

The control unit 11 can be programmed to intervene at the occurrence of any variation of the infusion fluid supply to the extracorporeal blood circuit, by changing the operating mode of the blood pump 1. This variation can be one or more variations selected in the group of variations including: a halt, a slow-down, a start, and a speed-up of the infusion fluid supply.

Figure 2:
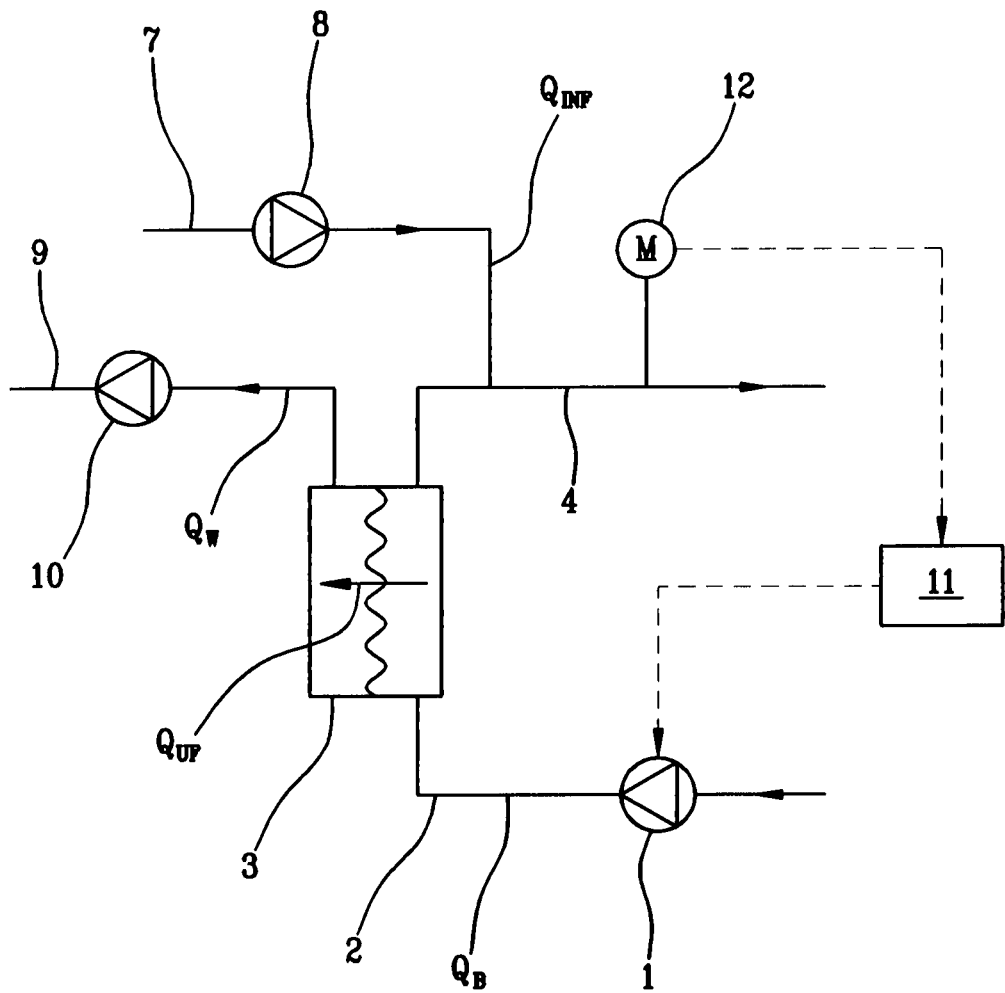
FIG. 2 is an hemofiltration apparatus according to the present invention.

FIG. 2 shows a hemofiltration apparatus according to the invention, in which the elements which are the same as in the apparatus of FIG. 1 have been denoted using the same reference numbers. The apparatus of FIG. 2 has substantially the same operation as the embodiment of FIG. 1, at least inasmuch as the aspects inherent to the present invention are concerned.

Figure 3:
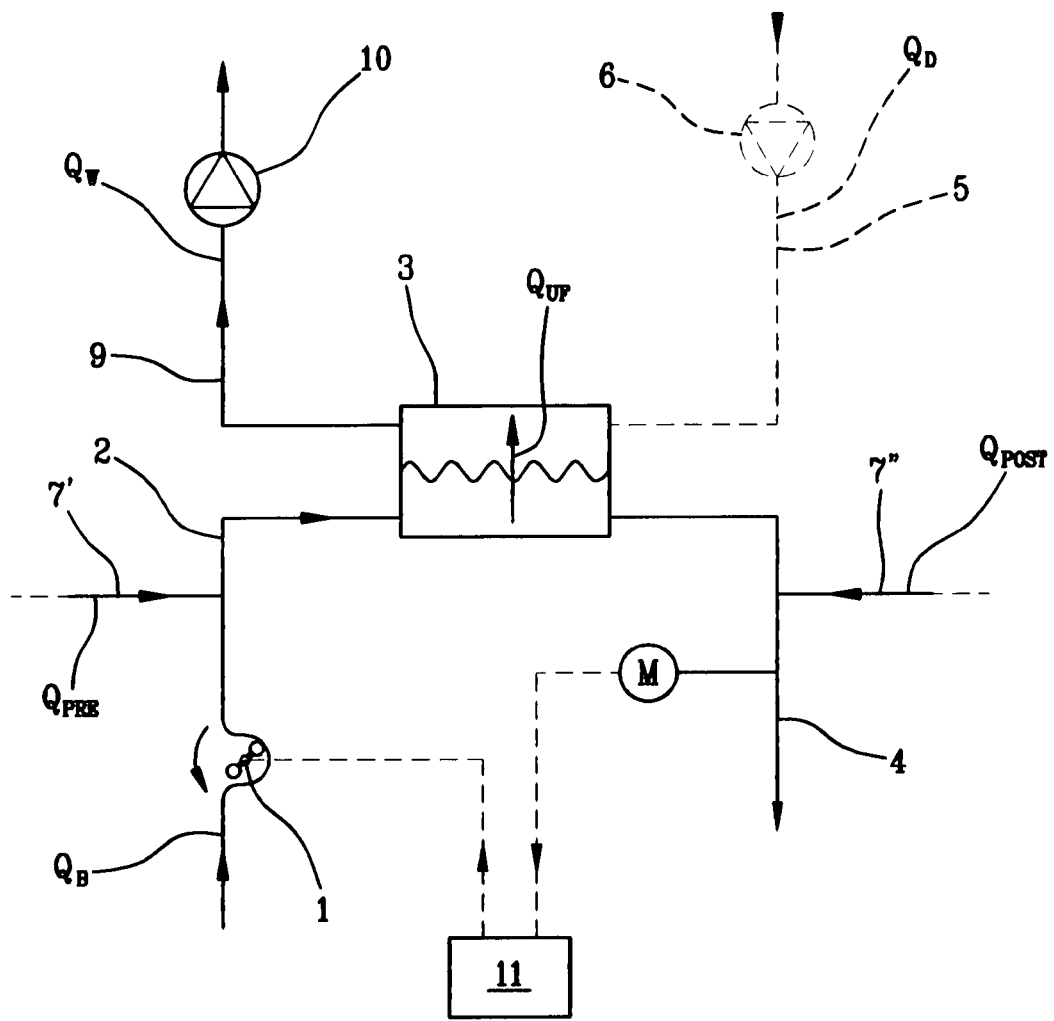
FIG. 3 is an hemo(dia)filtration apparatus according to the present invention.

FIG. 3 shows a hemo(dia)filtration apparatus according to the invention, in which the elements which are the same as in the apparatus of FIG. 1 or 2 have been denoted using the same reference numbers. The apparatus comprises, optionally, a dialysis fluid supply system providing the flow $Q_D$. The replacement fluid supply comprises a pre-dilution line 7' and/or a post-dilution line 7". The replacement fluid supply may comprise only one of the lines 7' and 7" or both. The replacement fluid supply comprises, optionally, a valve system for selectively closing one or both of the lines 7' and 7". The pre-dilution line 7' is configured to supply a flow $Q_{PRE}$ and the post-dilution line 7" is configured to supply a flow $Q_{POST}$. In this case $Q_{INF}=Q_{PRE}+Q_{POST}$. The replacement fluid source comprises a device for on-line preparation of the fluid and/or one or more batch sources. The pre- and post-dilution lines 7' and 7" may be separately connected to at least two separate fluid sources or may branch off from a supply line connected to a fluid source. The apparatus of FIG. 3 has substantially the same operation as the embodiment of FIG. 1 or 2, at least inasmuch as the aspects inherent to the present invention are concerned.

Several possible criteria or methods for controlling the switching of control modes for the blood pump have been described (e.g. operator intervention or timer settings). In a specific embodiment of the invention, the control unit of any one of the above described medical apparatuses is configured to control an automatic switch-over between a first control mode (e.g. the flow control mode) and the venous pressure control mode. This automatic control may comprise the following operations. When one of the aforementioned triggering situation occurs, the venous pressure feedback control function takes over the control of the blood pump speed and reduces the blood flow if the venous pressure exceeds a specified value (set point value or upper limit value or another threshold value). The pressure feedback controller then modulates the blood pump speed to keep the venous pressure at the desired limit. If the venous pressure drops below the high limit, the controller increases the blood pump speed until it reaches the user selected blood flow set point. The venous pressure feedback control is then disabled until next time the venous pressure exceeds the high limit value.

In a further embodiment, the blood pump venous pressure feedback control method and system can also be used to reduce pressure drops after a start of the infusion pump. In this case an increase of the blood pump speed may occur.

The above description states that the blood pump venous pressure feedback control method and system can be used to reduce pressure transients after start/stop of the infusion pump in hemo(dia)filtration post dilution. Additionally, or as an alternative, the blood pump venous pressure feedback control method and system can be used to reduce pressure transients after start/stop of the infusion pump in hemo(dia)filtration pre dilution, though these transients are generally smaller and considered less critical.

Furthermore the blood pump venous pressure feedback control method and system can be used, particularly in hemodialysis or hemo(dia)filtration, to reduce pressure transients after start of the infusion of an infusion bolus of a fluid into the blood path, wherein the infusion bolus includes a certain amount of infusion fluid which may be not balanced by a corresponding ultrafiltration of plasma.

The invention claimed is:

1. A hemodialysis or hemo(dia)filtration apparatus, comprising:
a blood treatment device having a blood chamber and a fluid chamber which are separated from one another by a semipermeable membrane;
an extracorporeal blood circuit having an arterial line for blood removal from an individual and a venous line for blood return to the individual, the arterial line and the venous line being connected to an inlet and, respectively, to an outlet of the blood chamber;
a blood movement device configured for moving the blood along the extracorporeal circuit;
at least a venous pressure sensor configured for emitting a venous pressure signal indicating a pressure in the venous line;
a fluid circuit having at least a discharge line connected to an outlet of the fluid chamber;
an ultrafiltration device configured for ultrafiltering plasmatic liquid from the blood chamber to the fluid chamber across the semipermeable membrane;
an infusion circuit having at least a first supply line of an infusion fluid connected to the extracorporeal blood circuit;
an infusion fluid supply device configured to provide a supply of the infusion fluid along the first supply line;
a control unit programmed to perform the following operations:
determining an occurrence of a halt or slow-down or start or speed-up of the supply of the infusion fluid to the extracorporeal blood circuit; and
passing from a first command mode of the blood movement device to a second command mode of the blood movement device by effect of said occurrence of a halt or slow-down or start or speed-up, wherein the blood movement device is, in the second command mode, controlled on a basis of a comparison between said venous pressure signal and at least a set point value.

2. The apparatus of claim 1, wherein the infusion circuit and the infusion fluid supply device are configured to supply a replacement fluid during a hemo(dia)filtration treatment.

3. The apparatus of claim 1, wherein the infusion circuit and the infusion fluid supply device are configured to supply a replacement fluid during an infusion bolus.

4. The apparatus of claim 1, wherein the first supply line is connected to the venous line or to the arterial line.

5. The apparatus of claim 1, wherein the determining of an occurrence of a halt or slow-down or start or speed-up comprises determining a halt or slow-down or start or speed-up of the infusion fluid supply device.

6. The apparatus of claim 1, wherein the control unit is programmed to cause a halt or slow-down or start or speed-up of the ultrafiltration across the semipermeable membrane, by effect of an occurrence of the halt or slow-down or start or speed-up of the supply of the infusion fluid.

7. The apparatus of claim 1, wherein the second command mode comprises controlling the blood movement device such that the venous pressure is controlled in a predetermined value range.

8. The apparatus of claim 1, wherein the second command mode is started up at a moment comprised in a predetermined time period which includes an occurrence of the halt or slow-down or start or speed-up of the supply of the infusion fluid.

9. The apparatus of claim 8, wherein the second command mode is started at a same moment of said halt or slow-down or start or speed-up of the supply of the infusion fluid.

10. The apparatus of claim 8, wherein the second command mode is started after a predetermined interval following, said halt or slow-down or start or speed-up of the supply of the infusion fluid.

11. The apparatus of claim 1, wherein the determining of a halt or slow-down or start or speed-up of the supply of the infusion fluid comprises detecting a signal supplied by a sensor indicating said halt or slow-down or start or speed-up of the supply of the infusion fluid.

12. The apparatus of claim 11, wherein said halt or slow-down or start or speed-up sensor is operatively associated to the infusion circuit and/or the infusion fluid supply device and/or the venous line and/or the extracorporeal blood circuit.

13. The apparatus of claim 11, wherein said halt or slow-down or start or speed-up sensor is configured to detect an operating parameter of the infusion fluid supply device.

14. The apparatus of claim 11, wherein said halt or slow-down or start or speed-up sensor is configured to detect a characteristic parameter of the infusion fluid and/or a mixture of the infusion fluid and the blood in the venous line or in the arterial line.

15. The apparatus of claim 1, wherein the first command mode comprises controlling the blood movement device in accordance with a second signal which is different from the venous pressure signal.

16. The apparatus of claim 15, wherein the second signal comprises a signal indicating the blood flow rate along the extracorporeal blood circuit.

17. The apparatus of claim 16, wherein the flow rate signal comprises a signal indicating an operating parameter of the blood movement device.

18. The apparatus of claim 1, wherein the fluid circuit has at least a supply line of a dialysis fluid connected to an inlet of the fluid chamber, and wherein the control unit is programmed to pass from the first command mode to the second command mode in consequence of a passage from a hemo(dia)filtration treatment mode to a hemodialysis treatment mode.

19. The apparatus of claim 1, wherein the set point value corresponds to a value of venous pressure measured on or before said halt or slow-down or start or speed-up of the supply of the infusion fluid.

20. A hemodialysis or hemo(dia)filtration apparatus, comprising:
- a blood treatment device having a blood chamber and a fluid chamber which are separated from one another by a semipermeable membrane;
- an extracorporeal blood circuit having an arterial line for blood removal from an individual and a venous line for blood return to the individual, the arterial line and the venous line being connected to an inlet and, respectively, to an outlet of the blood chamber;
- a blood movement device configured for moving the blood along the extracorporeal circuit;
- at least a venous pressure sensor configured for emitting a venous pressure signal indicating a pressure in the venous line;
- a fluid circuit having at least a discharge line connected to an outlet of the fluid chamber;
- an ultrafiltration device configured for ultrafiltering plasmatic liquid from the blood chamber to the fluid chamber across the semipermeable membrane;
- an infusion circuit having at least a first supply line of an infusion fluid connected to the extracorporeal blood circuit;
- an infusion fluid supply device configured to provide a supply of the infusion fluid along the first supply line;
- an event sensor configured for indicating an event selected in the group of:
  - a halt of the supply of the infusion fluid to the extracorporeal blood circuit,
  - a slow-down of the supply of the infusion fluid to the extracorporeal blood circuit,
  - a start of the supply of the infusion fluid to the extracorporeal blood circuit,
  - a speed-up of the supply of the infusion fluid to the extracorporeal blood circuit;
- a control unit programmed to perform the following operations:
  - determining an occurrence of said event by detecting an event signal supplied by said event sensor and indicative of said halt or slow-down or start or speed-up of the supply of the infusion fluid; and
  - passing from a first command mode of the blood movement device to a second command mode of the blood movement device by effect of said occurrence of said event, wherein the blood movement device is, in the second command mode, controlled on a basis of a comparison between said venous pressure signal and at least a set point value.

* * * * *